United States Patent
Gargiulo et al.

(10) Patent No.: US 10,182,727 B2
(45) Date of Patent: Jan. 22, 2019

(54) MONITORING PNEUMOCARDIAL FUNCTION

(71) Applicant: University of Western Sydney, Penrith, New South Wales (AU)

(72) Inventors: Gaetano Gargiulo, Kogarah (AU); Paul Breen, Redfern (AU)

(73) Assignee: WESTERN SYDNEY UNIVERSITY, Penrith NSW (AU)

( * ) Notice: Subject to any disclaimer, the term of this patent is extended or adjusted under 35 U.S.C. 154(b) by 94 days.

(21) Appl. No.: 15/100,234

(22) PCT Filed: Nov. 27, 2014

(86) PCT No.: PCT/AU2014/050380
§ 371 (c)(1),
(2) Date: May 27, 2016

(87) PCT Pub. No.: WO2015/077839
PCT Pub. Date: Jun. 4, 2015

(65) Prior Publication Data
US 2017/0000357 A1    Jan. 5, 2017

(30) Foreign Application Priority Data

Nov. 28, 2013 (AU) ................................. 2013904602

(51) Int. Cl.
*A61B 5/0205* (2006.01)
*A61B 5/06* (2006.01)
(Continued)

(52) U.S. Cl.
CPC ............ *A61B 5/02055* (2013.01); *A61B 5/01* (2013.01); *A61B 5/0205* (2013.01);
(Continued)

(58) Field of Classification Search
None
See application file for complete search history.

(56) References Cited

U.S. PATENT DOCUMENTS 4,308,872 A   1/1982   Watson et al.
4,960,118 A   10/1990  Pennock
(Continued)

FOREIGN PATENT DOCUMENTS

EP    1 731 094 A1   12/2006
EP    2 508 124 A2   10/2012
(Continued)

OTHER PUBLICATIONS

Supplementary European Search Report in related European Application No. EP 14 86 6300, dated Jun. 27, 2017.
(Continued)

*Primary Examiner* — Brian T Gedeon
(74) *Attorney, Agent, or Firm* — Knobbe, Martens, Olson & Bear, LLP

(57) ABSTRACT

A pneumocardial function monitor includes a carrier configured to be mounted about at least a part of a trunk of a body of a subject. A sensing arrangement is mounted on the carrier, the sensing arrangement including at least one element for monitoring changes in volume of the part of the subject's body. A signal processing module is in communication with the sensing arrangement for processing signals output from the sensing arrangement, the signal processing module having at least one output for outputting a signal related to respiratory function and/or cardiac function.

16 Claims, 13 Drawing Sheets

(51) Int. Cl.
*A61B 5/00* (2006.01)
*A61B 5/0408* (2006.01)
*A61B 5/08* (2006.01)
*A61B 5/01* (2006.01)
*A61B 5/113* (2006.01)

(52) U.S. Cl.
CPC .......... *A61B 5/04085* (2013.01); *A61B 5/067* (2013.01); *A61B 5/0806* (2013.01); *A61B 5/0809* (2013.01); *A61B 5/6805* (2013.01); *A61B 5/6831* (2013.01); *A61B 5/113* (2013.01)

(56) References Cited

U.S. PATENT DOCUMENTS

| | | | | |
|---|---|---|---|---|
| 5,178,151 | A * | 1/1993 | Sackner | A61B 5/1135 600/485 |
| 5,191,893 | A * | 3/1993 | Reiten | A61B 5/1135 600/534 |
| 6,626,842 | B2 * | 9/2003 | Oka | A61B 5/0285 600/526 |
| 7,094,206 | B2 * | 8/2006 | Hoffman | A61B 5/0809 600/529 |
| 8,668,653 | B2 | 3/2014 | Nagata et al. | |
| 8,945,328 | B2 * | 2/2015 | Longinotti-Buitoni | A61B 5/0002 156/234 |
| 9,002,427 | B2 * | 4/2015 | Tupin, Jr. | A61B 5/0507 600/407 |
| 9,492,105 | B1 * | 11/2016 | Kayyali | A61B 5/08 |
| 2002/0032388 | A1 * | 3/2002 | Kristbjarnarson | A61B 5/1135 600/538 |
| 2005/0240087 | A1 * | 10/2005 | Keenan | A61B 5/0205 600/301 |
| 2008/0027341 | A1 * | 1/2008 | Sackner | A61B 5/0205 600/509 |
| 2008/0300503 | A1 | 12/2008 | Lee et al. | |
| 2012/0029299 | A1 * | 2/2012 | Deremer | A61B 5/0002 600/300 |
| 2012/0136232 | A1 * | 5/2012 | Jeong | A61B 5/0002 600/388 |
| 2015/0018647 | A1 * | 1/2015 | Mandel | A61B 5/14552 600/323 |

FOREIGN PATENT DOCUMENTS

| | | |
|---|---|---|
| JP | S53-126786 A | 11/1978 |
| JP | 2009-525070 A | 7/2009 |
| WO | WO 99/064657 A2 | 12/1999 |
| WO | WO 2005/089645 A1 | 9/2005 |
| WO | WO 2007/089751 A2 | 8/2007 |

OTHER PUBLICATIONS

Office Action in related Japanese Application No. JP 2016-533542, dated Jul. 5, 2018.

* cited by examiner

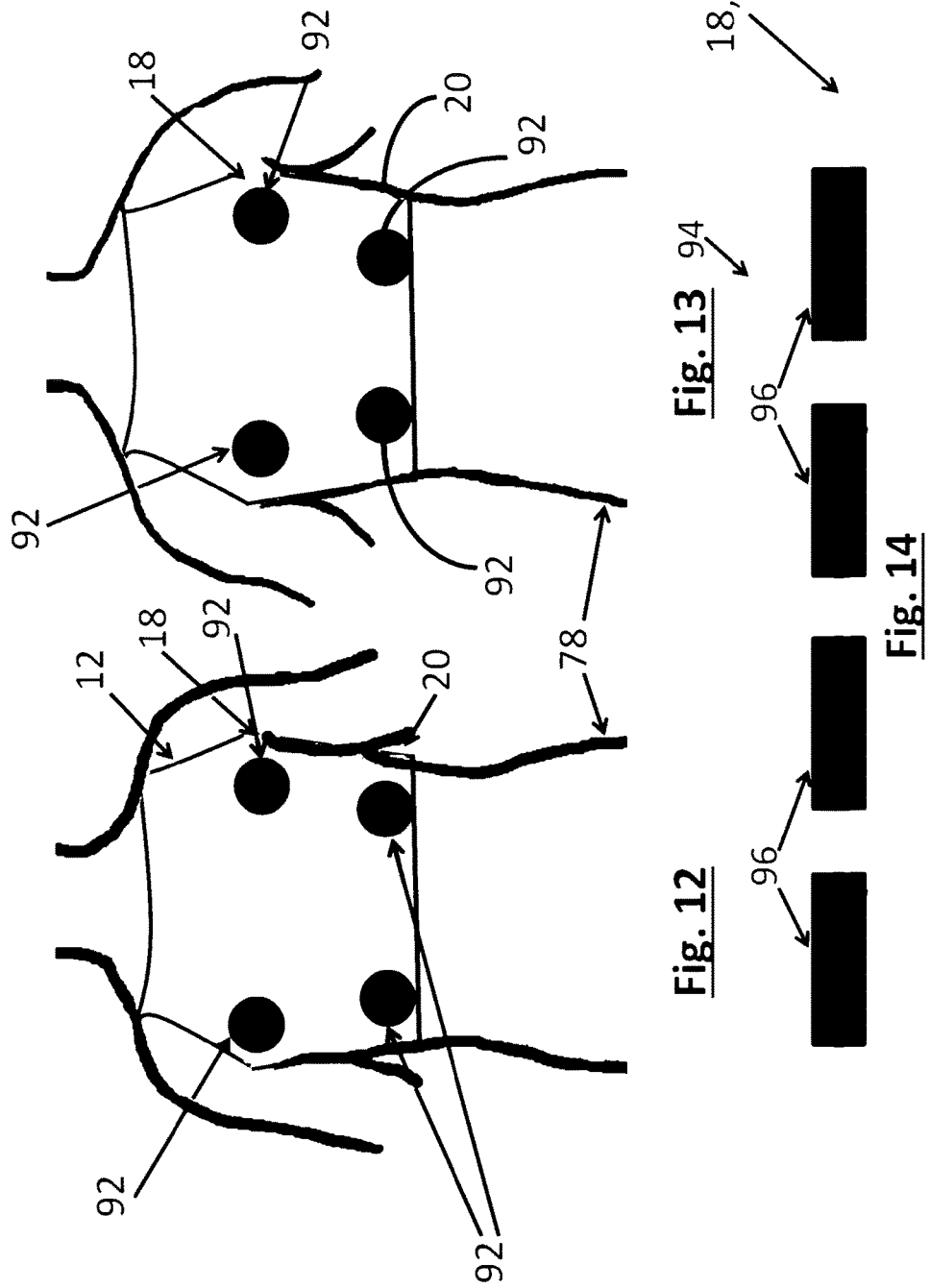

MONITORING PNEUMOCARDIAL FUNCTION

CROSS-REFERENCE TO RELATED APPLICATIONS

This application is a national phase application under 35 U.S.C. § 371 of International Application No. PCT/AU2014/050380, filed on Nov. 27, 2014, which claims the benefit of Australian Provisional Patent Application No 2013904602 filed on 28 Nov. 2013, the disclosures of which are incorporated herein by reference in their entirety.

TECHNICAL FIELD

This disclosure relates, generally, to the monitoring of pneumocardial function and, more particularly, to a pneumocardial function monitor and to a method of monitoring pneumocardial function.

In this specification, the term "pneumocardial" is to be understood to refer to cardiac and respiratory functions of a subject, the respiratory function relating to both lung and diaphragm functions.

BACKGROUND

Measurement of respiration effort is required to diagnose or monitor various diseases ranging from emphysema to sleep apnoea. Generally the devices used for measurement use some sort of mask which is cumbersome and is often inconvenient and uncomfortable for a subject to wear.

Also, variation of chest circumference at the diaphragm is a clear indication of respiration effort. It has been shown by electromyography (EMG) measurement that to diaphragm activity is linked with sleep apnoea.

In some cases it is useful to monitor cardiac function in addition to respiratory function.

SUMMARY

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to a first aspect of the disclosure, there is provided a pneumocardial function monitor which includes:
a carrier configured to be mounted about at least a part of a trunk of a body of a subject;
a sensing arrangement mounted on the carrier, the sensing arrangement comprising at least one element for monitoring changes in volume of the part of the subject's body; and
a signal processing module in communication with the sensing arrangement for processing signals output from the sensing arrangement, the signal processing module having at least one output for outputting a signal related at least to respiratory function.

In this specification, the term "subject" is to be understood as referring to human and non-human subjects unless the context clearly indicates otherwise. For non-human subjects, the disclosure may be particularly, but not necessarily exclusively, applicable to animals where monitoring respiratory effort and/or cardiac function could be beneficial. A non-limiting example of such an application is racehorses.

The signal processing module may have at least two outputs, a first output for outputting the signal related to respiratory function and a second output for outputting a signal related to cardiac function.

The carrier may be configured to insulate the sensing arrangement from the subject's skin.

The sensing arrangement may comprise a plurality of sensing elements which operate together to monitor at least respiratory function. At least one sensing element of the plurality of sensing elements may also monitor cardiac function.

The sensing arrangement may include a first sensing mechanism comprising a pair of resistive bands arranged in spaced relationship. Further, the sensing arrangement may include a second sensing mechanism comprising a helically arranged band carried by the carrier. The helically arranged band may be an electro-resistive band.

Each band may be of a resiliently flexible material, resistivity of the bands increasing with extension. Each band may be extended at rest to provide a resting resistance.

The signal processing module may include a filter for filtering out artefact signals. "Artefact signals" are to be understood as any signals which are not of interest such as noise signals. Also, in the case of measuring cardiac function, the first output signal related to respiratory function may be treated as an artefact signal.

The signal processing module may include amplification circuitry to amplify signals from the sensing arrangement. In this regard, the signals in the bands of the sensing arrangement are maintained at a level below a micro-shock threshold, being about 200 µA or about 10 µA for ambulatory subjects and surgery room subjects, respectively.

The sensing arrangement may include a position detecting unit for monitoring a position of the body of the subject. Further, the sensing arrangement may include a temperature monitoring mechanism for monitoring core temperature of the body of the subject. In addition, the sensing arrangement may include an acoustic sensing component for sensing sounds emitted by the subject.

According to a second aspect of the disclosure, there is provided a method of monitoring pneumocardial function, the method including:
mounting at least one sensing element about a part of a trunk of a body of a subject;
using the at least one sensing element to monitor variations in volume of the part of the subject's body;
processing data output by the at least one sensing element; and
outputting a signal relating at least to respiratory function.

The method may include processing the data to output a further signal relating to cardiac function.

The method may include mounting a plurality of sensing elements about the part of the subject's body, the sensing elements being configured to monitor both respiratory function and cardiac function.

The method may include monitoring changes in resistivity of the sensing elements to obtain data on at least one of respiratory function and cardiac function.

BRIEF DESCRIPTION OF DRAWINGS

An embodiment of the disclosure is now described by way of example with reference to the accompanying drawings in which.

FIG. 12 shows a front view of yet a further embodiment of a sensing arrangement of the monitor;

FIG. 13 shows a rear view of the embodiment of the sensing arrangement of the monitor of FIG. 12;

FIG. 14 shows a schematic representation of an alternative embodiment to that of the embodiment shown in FIGS. 12 and 13;

DETAILED DESCRIPTION OF EXEMPLARY EMBODIMENTS

Figure 1:
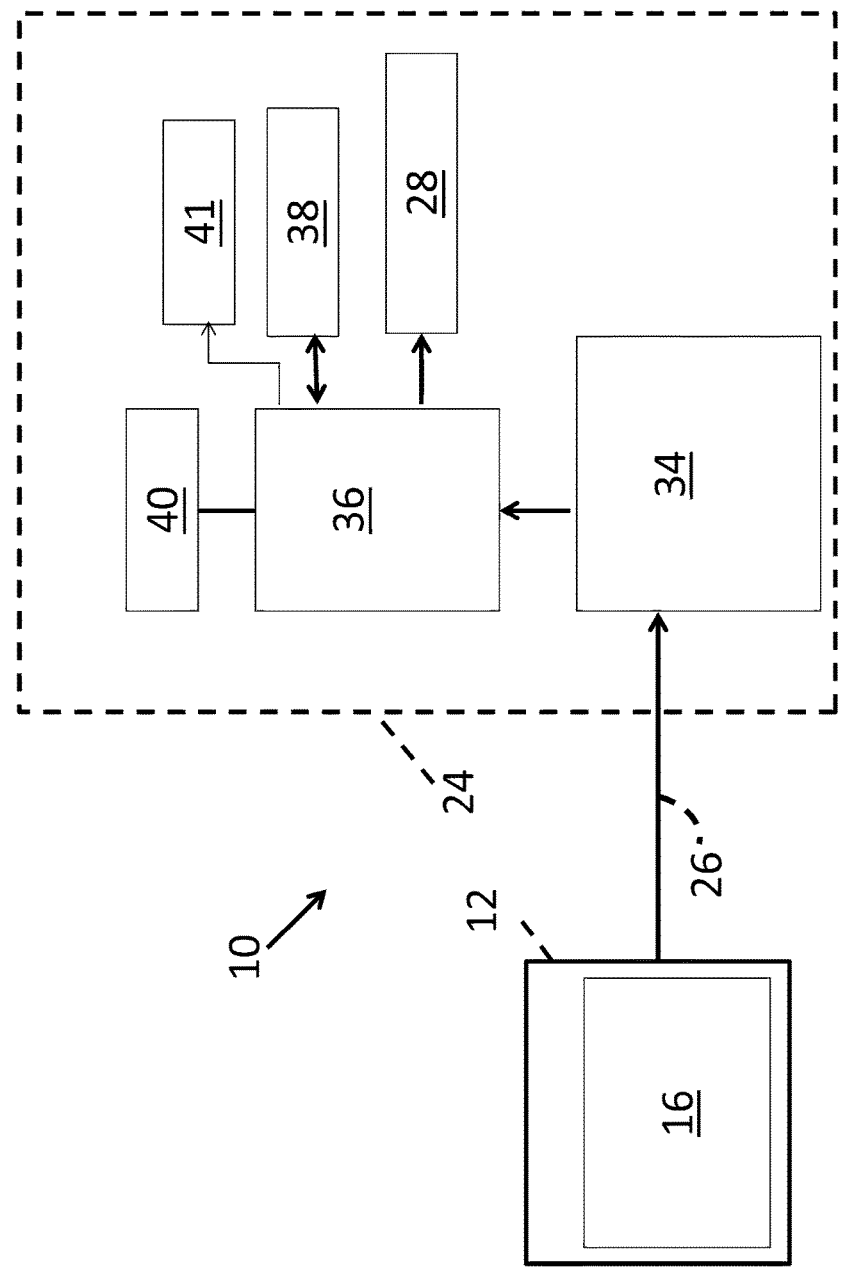
FIG. 1 shows a schematic block diagram of an embodiment of a pneumocardial function monitor.

Referring initially to FIG. 1 of the drawings, reference numeral 10 generally designates a schematic block diagram of an embodiment of a pneumocardial function monitor. The monitor 10 comprises a carrier 12 configured to be mounted about at least a part of a trunk of a body of a subject. More particularly, the carrier is mountable about at least the thorax of the subject, as represented by the skeletal part 14 in FIG. 4 of the drawings. In this specification, the thorax is to be understood to include the subject's diaphragm.

A sensing arrangement 16 is mounted on the carrier 12, the sensing arrangement 16 comprising a plurality of elements, or bands, 18, 20 and 22 (FIG. 4) for determining changes in volume of the subject's thorax 14.

A signal processing module 24 is in communication with the sensing arrangement 16, as indicated schematically by arrow 26 in FIG. 1 of the drawings. The signal processing module 24 processes signals output from the sensing arrangement 16 and the signal processing module 24 has at least one communications output line 28 for outputting a signal related at least to respiratory function.

The carrier 12 can adopt various forms but, in an embodiment, is in a form which can be worn by the subject. Thus, for example, the carrier 12 is in the form of a T-shirt (as shown schematically in FIG. 4 of the drawings), vest, singlet, or the like, which fits snugly at least around the thorax 14 of the subject but insulates the subject from the sensing arrangement 16. The carrier 12 ensures that the sensing arrangement 16 is maintained in close abutment with the thorax 14 of the subject due to the tight fitting nature of the carrier 12.

Figure 4:
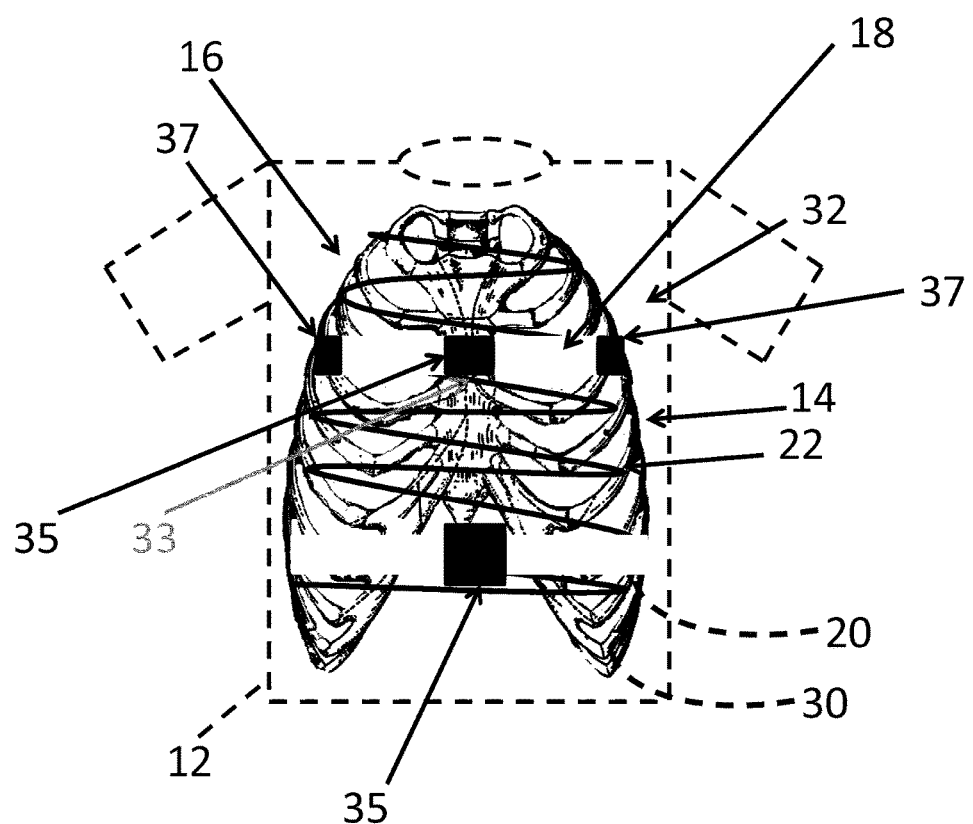
FIG. 4 shows a schematic representation of a sensing arrangement of the monitor.

In the embodiment shown in FIG. 4 of the drawings, the sensing arrangement 16 comprises a pair of spaced electro-resistive bands 18 and 20. The bands 18, 20 are suitably spaced apart to approximate the volume of the subject's thorax 14. The band 18 is positioned just above an imaginary line defined by a line along which precordial leads for an ECG are normally arranged on the thorax 14. The operatively lower band 20 is positioned just below the subject's diaphragm (not shown) over the floating ribs of the subject's rib cage 30. With this arrangement, changes in volume of the subject's thorax can be determined and output by the signal processing module 24 to enable changes in volume of the thorax 14 to be monitored and output by the signal processing module 24.

The band 22 is a helically coiled band and is carried by the carrier 12 to be placed about the subject's thorax 14 with the upper part of the band 22 more closely approximating the upper part of the subject's lungs 32. Hence, the helically coiled band 22 can ideally be used by the monitor 10 for monitoring the volume of the lungs 32 of the subject.

As indicated above, each of the bands 18, 20 and 22 is an electro-resistive device. Such a device is one where resistance increases with extension. The bands 18, 20 and 22 are mounted in or on the carrier 12 in a manner that each band 18, 20 and 22 is slightly extended in its rest position to have a low resistance value at rest. The "at rest" resistance value of the band 18, 20, 22 is a manufacturing parameter to be specified. Typically, the "at rest" resistance is about 10 kΩ or less.

It is also to be noted that, due to the nature in which the bands 18, 20 and 22 are "driven" to obtain a response and due to the fact that the bands 18, 20 and 22 are isolated from the body of the subject, the sensitivity of the chest band 18 is such that cardiac signals due to the subject's heartbeat can also be detected by the band 18 and output via the signal processing module 24 on its communications output line 28.

The sensing arrangement 16 of the monitor 10 includes a position detecting mechanism 33 comprising a plurality of triaxial accelerometers 35, one accelerometer 35 being arranged on each of the bands 18 and 20 and/or on spaced turns of the band 22. The accelerometers 35 are arranged on the bands 18, 20 and/or 22 so as to be positioned, in use, substantially aligned with a sternum of the subject. The position determining mechanism 33 may be implemented in other forms including gyroscopes, magnetometers, or the like, or combinations of such devices to provide further benefits such as greater dynamic accuracy.

The accelerometers 35 are used to monitor the position of the body of the subject and movement of the subject's body while undergoing monitoring. The accelerometers 35 are also used for artefact removal which may occur, for example, when the subject's body undergoes abrupt movement, for example, when playing sport.

The sensing arrangement 16 of the monitor 10 further includes a temperature monitoring mechanism comprising a pair of temperature sensors 37 arranged in spaced relationship on the band 18. The temperature sensors 37 are positioned on the band 18 to be located below the armpits of the subject, in use. The temperature sensors 37 provide an indication of core temperature and provide useful information during sleep studies and during sporting activities or other activities when the subject is exerted.

The signal processing module 24 monitors the temperature from each of the temperature sensors 37 and takes the average of the temperature readings for its analysis.

The signal processing module 24 comprises signal conditioning circuitry 34, an output of which is fed to a processing module, or processor, 36. Output signals from the processor 36 are output on the communications output line 28. In addition, the signal processing module 36 includes a data storage module 38 as well as a battery 40.

The data storage module 38 includes at least one removable data storage device (not shown) for storing recorded long term data (for example, sleep data). The removable data storage device is removed from the monitor 10 for subsequent off-line study and analysis.

In an embodiment, the battery 40 is a rechargeable battery such as a lithium-ion battery. The battery 40 is configured such that it will not operate when a charge cord is connected unless the charger is a medically approved, suitably isolated charger. The battery includes a proprietary non-standard connector which requires it to be removed for recharging.

The signal processing module 24 further includes a discernible alarm unit 41. The alarm unit 41 is configured either by the subject or by clinical staff to generate an alarm signal, for example, an audible and/or a visual alarm, when an alarm condition occurs. An example of an alarm condition is prolonged apnoea.

Signals of interest detected by the sensing arrangement 16 can be captured in one of two ways, either via a voltage driving/current sensing arrangement or via a current driving/voltage sensing arrangement. As indicated, in both scenarios, the sensing bands 18, 20 and 22 should be isolated from the subject's body to avoid contact with the body.

Figure 2:
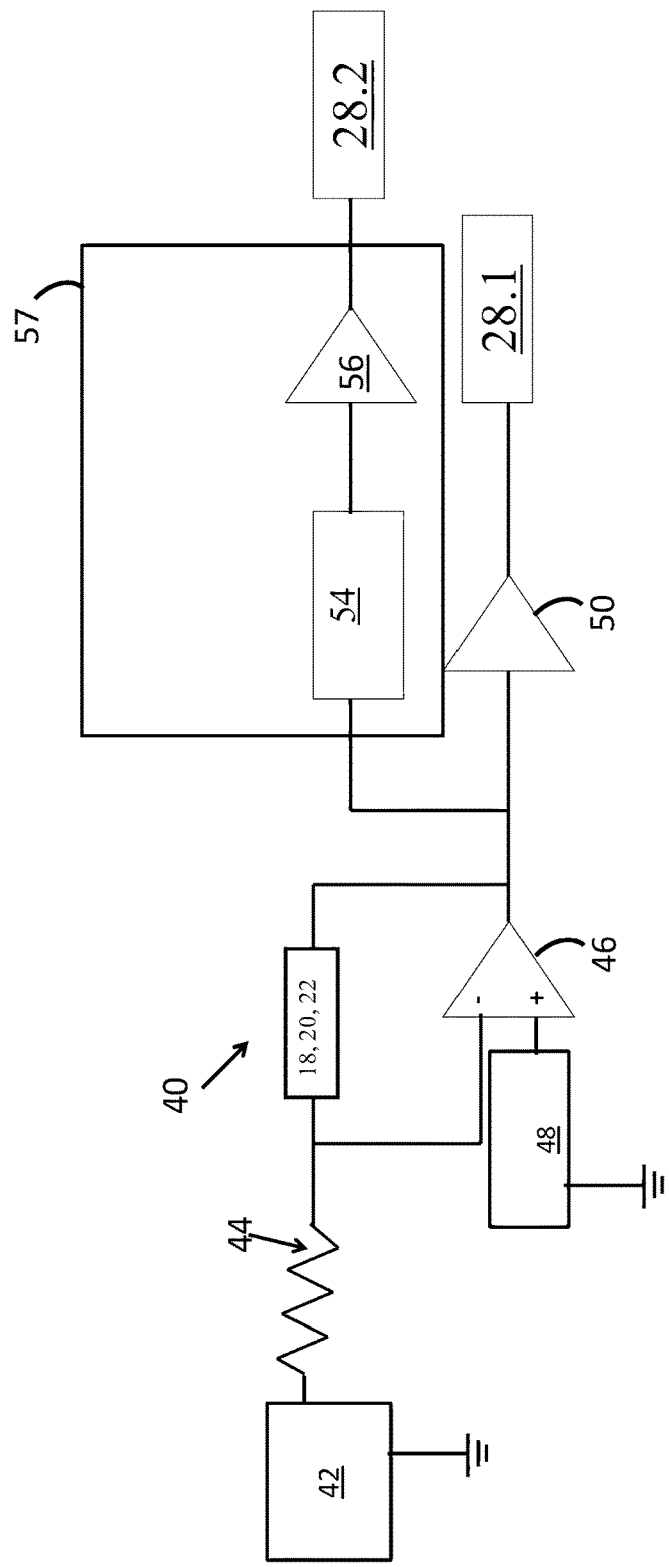
FIG. 2 shows a simplified circuit diagram of one implementation of the monitor.

Referring to FIG. 2 of the drawings, an embodiment of a voltage driving arrangement is illustrated and is designated generally by the reference numeral 40. The voltage driving arrangement comprises a constant voltage generator 42 feeding the associated band 18, 20, 22 via a resistor 44. The resistor 44 has a resistance value which is lower than that of the resistance of its associated bands 18, 20 or 22 when that band 18, 20, 22 is at rest. The resistor 44 operates as a feedback operator of an operational amplifier 46 to form a variable gain amplifier. The gain of the amplifier 46 is determined by the following equation:

$$\text{Gain}_{amp} = \frac{R_{resting} + \Delta R}{R_{Sensor}}$$

where:
$R_{resting}$ is the resistance of the band 18, 20, 22 at rest,
$\Delta R$ is the variation of resistance due to extension of the band 18, 20, 22, and
$R_{Sensor}$ is the value of the resistor 44.

A reference voltage 48 is fed to a non-inverting input of the amplifier 46. The amplifier 46 amplifies, with variable gain, the difference between the driving voltage output from the voltage generator 42 and the reference voltage 48. The reference voltage 48 is selected so that the output of the amplifier 46 for a relaxed, non-extended band 18, 20, 22 is very small but detectable. In other words, the reference voltage 48 should minimally affect the dynamics of the amplifier 46 but be greater than the noise and offset value of the amplifier 46. A reasonable value for the reference voltage is be about 1/20 the value of the dynamic range of the amplifier. Hence, for example, if the amplifier 46 had a dynamic range of 10V, the reference voltage 48 is set to be a fixed 0.5V at rest.

An output from the amplifier 46 is fed to an operational amplifier 50 operating as an active, low pass filter having a cut-off frequency of less than about 40 Hz. The output from the low pass filter 50 is fed to a first output 28.1 of the communications output line 28 of the signal processing module 24 and provides a signal representative of volume changes of the thorax 14 of the subject. An approximation of the volume changes is shown as the sine-waveform at 52 in FIG. 5 of the drawings.

The output from the amplifier 46 is also fed via a high pass filter 54 to a second operational amplifier 56 configured, once again, as a low pass filter having a cut-off frequency of less than about 40 Hz. The high pass filter 54 has a cut-off frequency of less than 1 Hz, more particularly, about 0.67 Hz to filter out volumetric changes of the thorax 14 and to provide, as an output on output line 28.2 of the communications output line 28 of the signal processing module 24, data relating to cardiac events. Examples of these cardiac events are shown by arrows 58 in FIG. 5 of the drawings. FIG. 6 shows, on an enlarged scale, a part of the waveform of FIG. 5 with the cardiac events 58 highlighted.

Instead of the discrete high pass filter 54 and low pass filter 56, the components 54 and 56 could be implemented as an active band pass filter (as shown by block 57) with the lower and upper frequency cut-off limits specified above.

Figure 3:
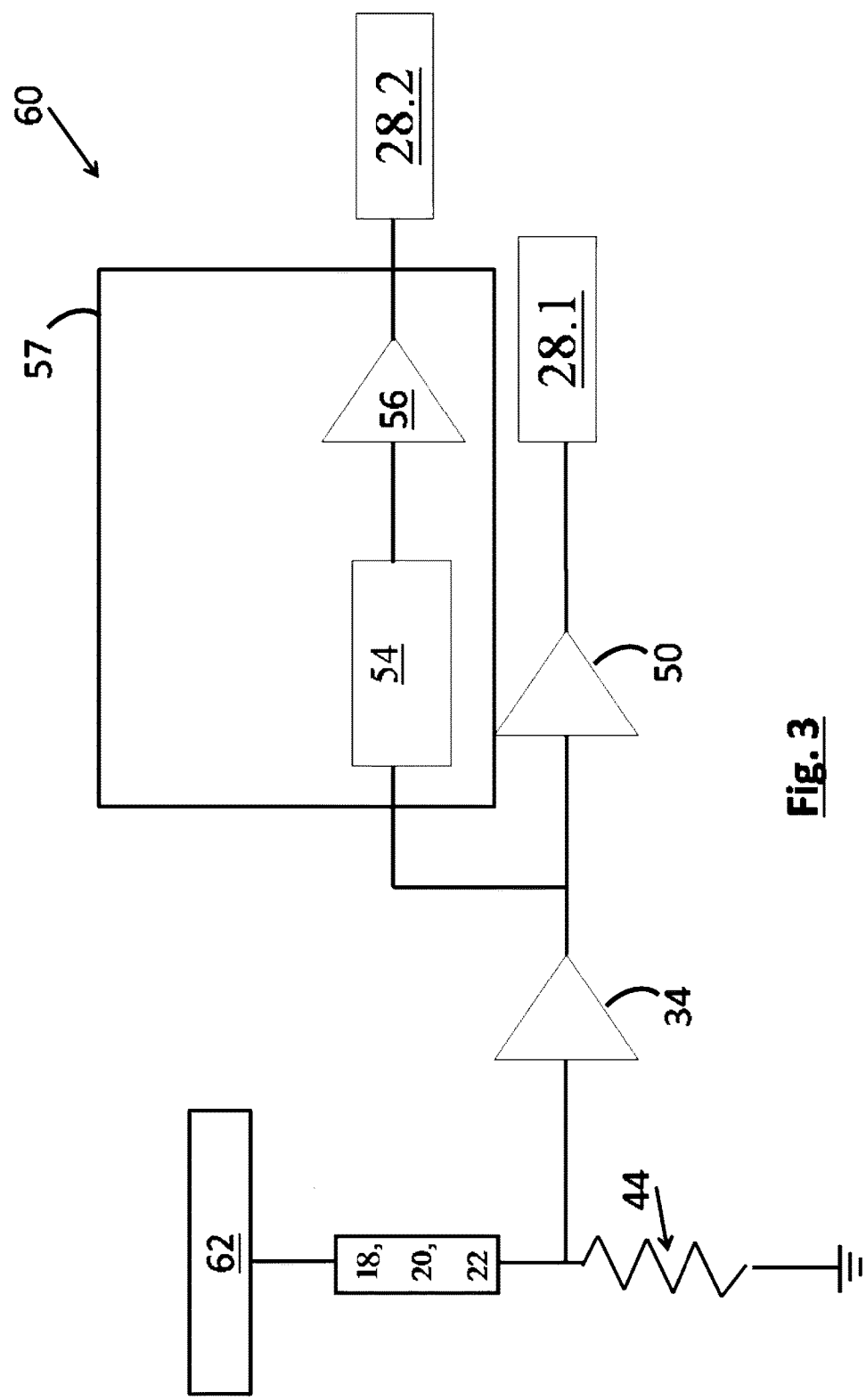
FIG. 3 shows a simplified circuit diagram of another implementation of the monitor.

Referring now to FIG. 3 of the drawings, a current driver arrangement for driving the bands 18, 20, 22 is illustrated and is designated generally by the reference numeral 60. With reference to FIG. 2 of the drawings, like reference numerals refer to like parts unless otherwise specified.

In this embodiment, the current driver arrangement 60 includes a constant current generator 62 which provides excitation signals to the bands 18, 20, 22.

In this current driver arrangement 60, a variable voltage is present across the resistor 44. This variable voltage is dependent on the extension of the relevant band, 18, 20 or 22 and the voltage is defined by the following equation:

$$V = \frac{R_{Sensor}}{R_{Sensor} + R_{resting} + \Delta R} I_{generator} \cong \frac{1}{2 + \Delta R} I_{generator}$$

where:—
$I_{generator}$ is the output current of the constant current generator 62 and the other equation terms have the same meanings as given above.

The approximation is valid if the value the resistor 44 is approximately equal to the resistance of the relevant band 18, 20, 22 when that band 18, 20 or 22 is in its rest condition.

Because the signal output by the relevant band 18, 20, 22 has high impedance, the current driver uses a high input impedance buffer as the signal conditioning circuit 34.

The remainder of the current driver arrangement 60, downstream of the output of the signal conditioning circuit 34 is the same as that described above with reference to FIG. 2 of the drawings.

Common to both the voltage driver arrangement 40 and the current driver arrangement 60 is that, in both implementations, adequate filtering and amplification reeds to be provided by the signal conditioning circuit 34 of the signal processing module 24. Amplification is required because the current circulating within each band 18, 20 or 22 must be contained below a micro-shock threshold which is restricted to 200 μA for ambulatory subjects and 10 μA for non-ambulatory subjects.

Filtering is also required to separate volume measurements from the pulse measurements in the case of the band 18.

The outputs 28.1 of both arrangements 40, 60 is a directly amplified sensor output which is DC coupled. The output 28.2, in contrast, is derived from an AC coupled active filter which separates the pulses from the volumetric output.

Thus, the 0.67 Hz frequency chosen for the filter 54 is selected based upon standard respiration suppression filters adopted in ECG and pulse monitors.

The cut off frequency for the low pass filter 50 and 56 is selected to be lower than a power line frequency to minimise power line noise and to avoid aliasing noise. Each of the filters 50, 54 and 56 is a first order filter to avoid signal phase distortion.

In use, the monitor 10 is initially calibrated. Calibration is achieved against a known volume using at least two values by linear sensor approximation. Fine tuning of the calibration can be achieved by wearing the monitor 10 during a spirometry examination which the subject is undergoing. From these data, the exact maximum lung volume of the subject can then be used by the software of the monitor 10 as a parameter for fine calculation of lung/air volume flow during respiration.

Another method for calibrating the monitor 10 is the use of a portable spirometer. This allows for fine calibration of the monitor 10. The subject blows into the spirometer a number of times, for example, three times and the value of the measured lung volume is used to calibrate chest volume variation measured by the bands 18, 20 and 22. The signal resulting from the sum of the resistance variations detected by each band 18, 20 and 22 can be directly calibrated via the reading from the spirometer.

Figure 5:
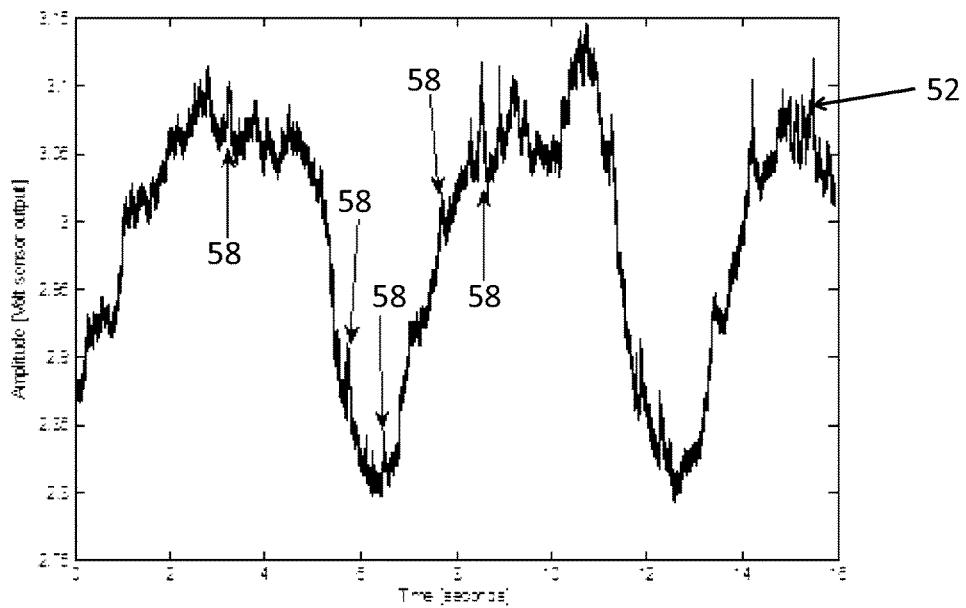
FIG. 5 shows a graphical representation of an output of a signal processing module of the monitor.
Figure 6:
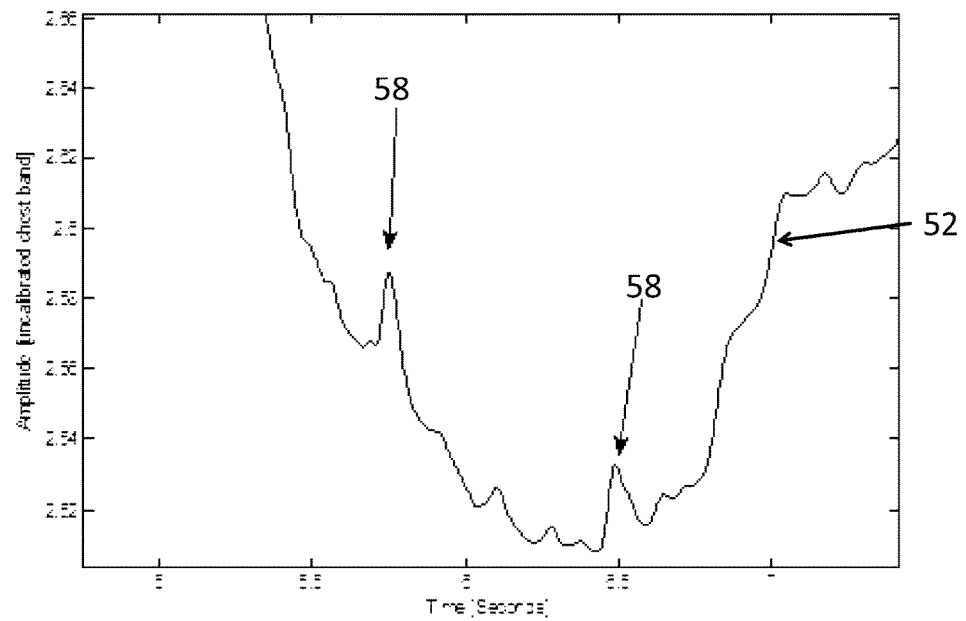
FIG. 6 shows a graphical representation of another output of the signal processing module of the monitor.

In this regard, it is to be noted that the sensor bands 18, 20 and 22 are sufficiently sensitive to enable lung/air volume flow during respiration to be measured as well as, in the case of the band 18, cardiac events as shown in FIGS. 5 and 6 of the drawings.

In addition, the provision of the accelerometers 35 facilitates the removal of artefact signals which arise due to sudden movements of the subject, either when the subject is very active or due to sudden movements while sleeping. This further improves the sensitivity of the monitor 10.

Figure 7:
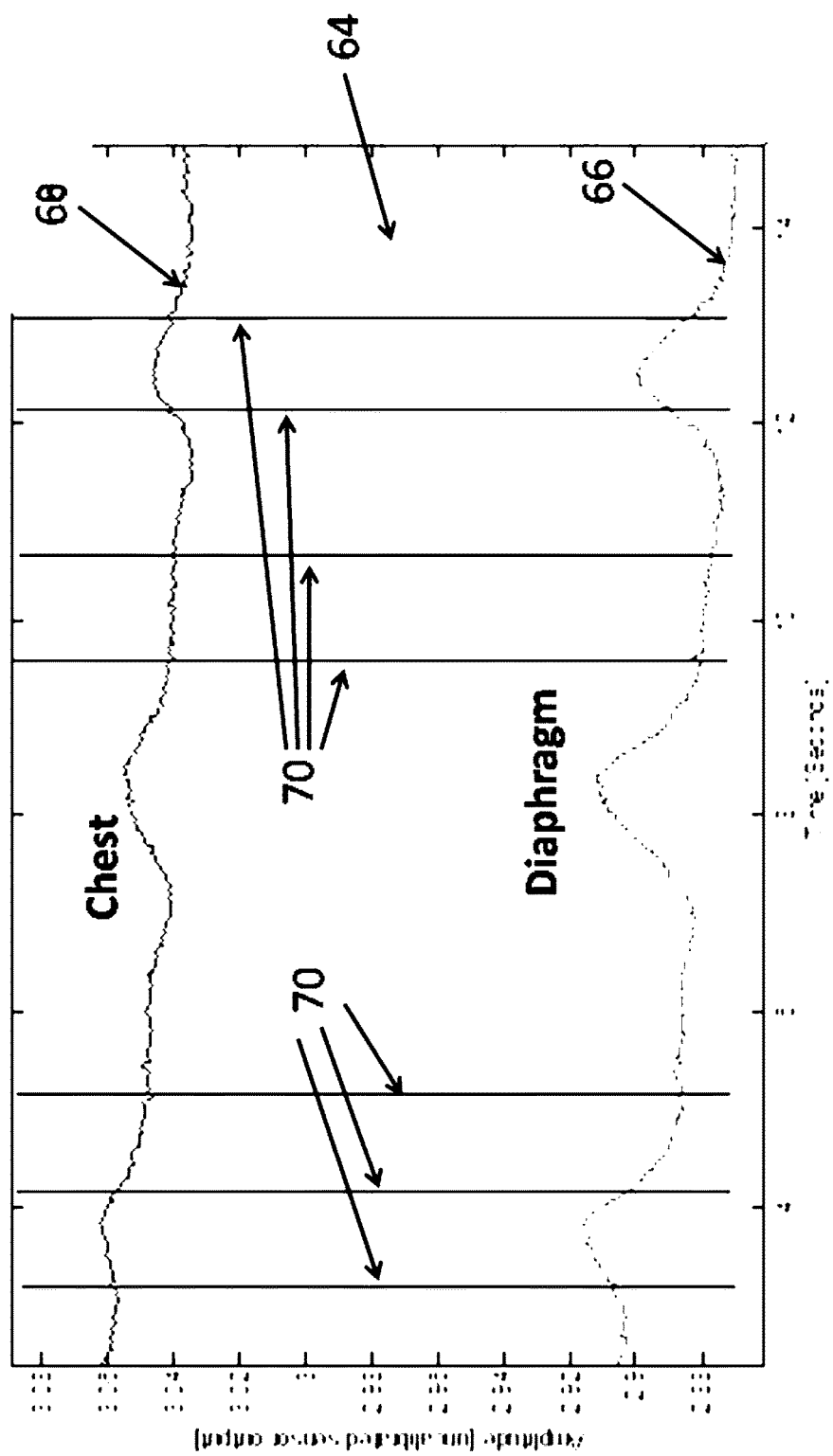
FIG. 7 shows a graphical representation of respiratory function and cardiac function as measured by the monitor of FIG. 1.

FIG. 7 of the drawings shows a graphic representation of signals measured by the monitor 10, these signals being designated generally by the reference numeral 64.

In this graph, a lower trace 66 shows volumetric changes in a diaphragm of the subject whereas an upper trace 68 shows variations in lung or chest volume of the subject. The vertical lines 70 represent cardiac events. In particular, the lower band 20 and the upper band 18 both contribute to the trace 68 whereas the lower band 20 and the helical band 22 both contribute to the trace 66. Cardiac events are measured by the band 18 alone. The data of the graph 64 are used to interpret respiratory effort based on variations of chest circumference at the diaphragm as indicated by the trace 66.

It has been shown, by EMG measurements, that low diaphragm activity is linked directly with sleep apnoea. Hence, a combination of respiration volume and activation of the diaphragm of the subject gives a unique observation of the degree of apnoea. Currently, this is only observable with a mask which is extremely cumbersome and uncomfortable for a subject and also disrupts the subject's sleeping patterns.

The accelerometers 35 enable the position of the subject's body to be monitored during sleep studies. In addition, the position of the subject's chest/diaphragm in the gravity field is able to be monitored using the accelerometers 35. In this regard, it is known that torsion of the subject's thoracic region may lead to increased respiratory effort and the provision of the accelerometers 35 arranged on each of the bands 18 and 20 so as to be spaced from each other facilitates measurement of such torsion.

In addition to volumetric measurements, as described above, the band 18 of the monitor 10 is used for measuring cardiac function. Vibrations from the heart impressed on the thorax 14 by the beating cardiac muscle are captured by the band 18 of the monitor 10 and are output via the signal processing module 24 of the monitor 10. Measured cardiac events may include: heart rate, heart rate variability and cardiac stroke output. Particularly the latter will be used in combination with air intake as indices of performance of the pneumocardial system during sleep or physical activity.

Figure 9:
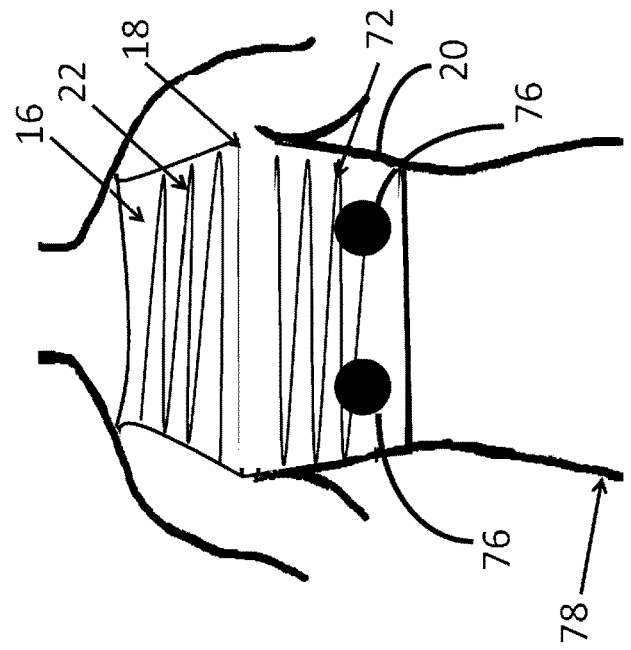
FIG. 9 shows a rear view of the embodiment of the sensing arrangement of the monitor of FIG. 8.
Figure 8:
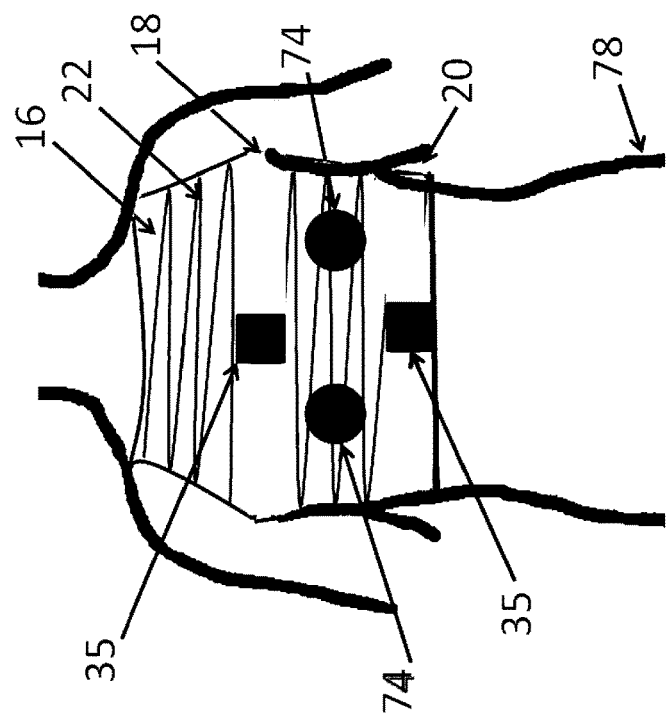
FIG. 8 shows a front view of another embodiment of a sensing arrangement of the monitor.

Referring now to FIGS. 8 and 9 of the drawings, another embodiment of the sensing arrangement of the sensing arrangement 16 of the monitor 10 is illustrated. With reference to the previous drawings, like reference numerals refer to like parts unless otherwise specified.

In this embodiment, the sensing arrangement includes an acoustic sensing component 72 comprising a plurality of acoustic sensors 74, 76. More particularly, two sensors 74, laterally spaced from each other, are anteriorly arranged, in use, on a subject 78 and two sensors 76, laterally spaced from each other, are posteriorly arranged, in use, on the subject 78.

The sensors 74 are arranged superiorly relative to the sensors 76. The sensors 74 are positioned on the carrier 12 so as to be located, in use, approximately midway between the heart and the diaphragm of the subject 78. The sensors 76 are arranged on the carrier 12 so as to be positioned proximate the lower lung region of the subject 78.

The acoustic sensing component 72 is for monitoring sounds emitted by the subject. While the prime purpose is to monitor coughing by the subject 78, the acoustic sensing component 72 could be used for monitoring other sounds emitted by the subject 78 such as, for example, as a result of the subject snoring.

There are different types of coughs, each having its own unique sounds and chest movements. The arrangement of the sensors 74, 76 of the acoustic sensing component 72 of the monitor 10 is able to provide information about the nature of the subject's cough, lung function during coughing, differentiation (i.e. which side and pulmonary lobe of the lung is affected), process of maturation (from a dry type cough to a wet type cough or vice versa), efficacy of treatment and/or efficacy of medication.

The signal processing module 24 is programmed to detect and monitor coughing by the subject 78 by detecting sudden variations in movement using the bands 18, 20 and 22 and the acoustic monitoring component 72. In general, respiration produces rhythmic movement and sounds which may vary depending on physical activity and state of health of the subject 78. Abrupt high frequency variations in both sound and movement (volume) as detected by the sensing arrangement 16 (including the accelerometers 35) is processed by the signal processing module 24 as a coughing event. Further, the signal processing module 24 is able, using a classification algorithm, to discriminate between variations in sounds and movement to determine the type of coughing event.

Figure 11:
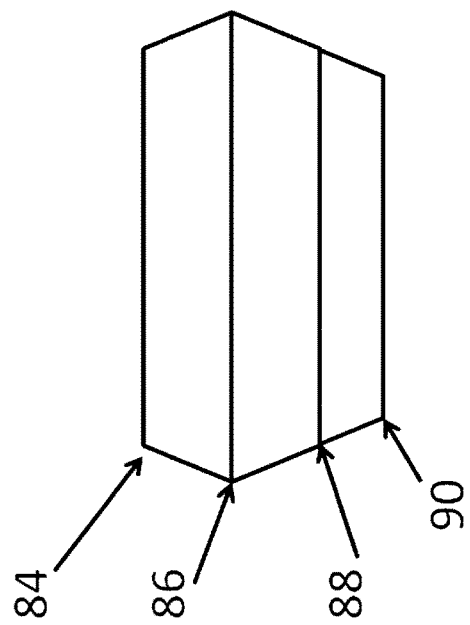
FIG. 11 shows a schematic representation of an approximation of the sensing arrangement of FIG. 10.
Figure 10:
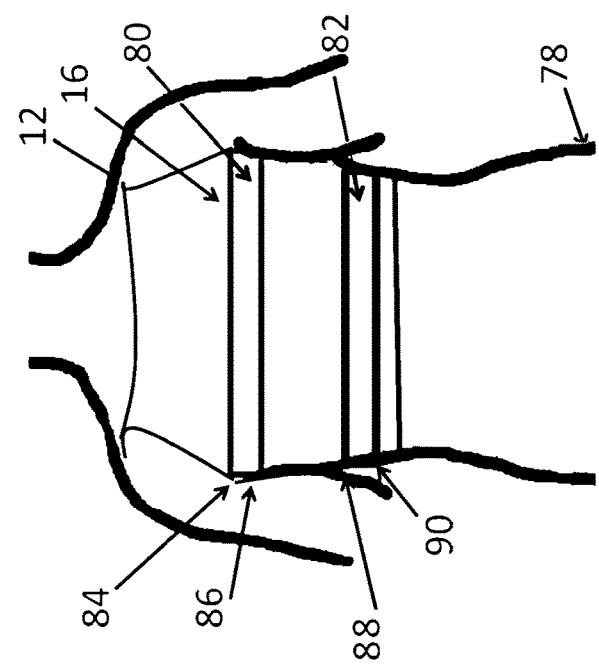
FIG. 10 shows a front view of a further embodiment of a sensing arrangement of the monitor.

Referring now to FIGS. 10 and 11 of the drawings, a further embodiment of the sensing arrangement 16 is shown. With reference to FIGS. 8 and 9 of the drawings, like reference numerals refer to like parts unless otherwise specified.

In this embodiment, the carrier 12 includes upper and lower band-like sub-carriers 80 and 82. The upper sub-carrier 80 is shaped to be received under the armpits of the subject 78 and the lower sub-carrier 82 is shaped to be received over the diaphragm of the subject 78. The upper sub-carrier 80 carries a pair of spaced electro-restrictive bands 84 and 86. Similarly, the lower sub-carrier 82 carries a pair of spaced electro-restrictive bands 88 and 90.

Having multiple electro-resistive bands 84, 86, 88 and 90 allows for a more accurate approximation of the shape of the trunk/thorax of the subject 78. The shape of the thorax is approximated as the sum of a number of small truncated cone volumes. An upper and a lower bound of each truncated cone is provided by the relevant bands 84, 86, 88 and 90, as the case may be. Hence, in the illustrated embodiment, the shape of the thorax is approximated by three truncated cones. These are a first truncated cone defined between bands 84 and 86, a second truncated cone defined between bands 86 and 88 and a third truncated cone defined between bands 88 and 90 as shown in FIG. 11 of the drawings.

Referring now to FIGS. 12-14 of the drawings, two other embodiments of the sensing arrangement 16 are shown. Once again, with reference to previous embodiments, like reference numerals refer to like parts, unless otherwise specified.

As described, the monitor 10 is for use in, for example, monitoring sleep disorders or respiratory/cardiac function of a subject engaged in physical activity. The possibility exists that, during sleep or a physical activity, a part of one of the bands 18 or 20 could become trapped against the subject's body resulting in incomplete extension of the band 18, 20. This adversely affects readings from the bands 18, 20 and can result in inaccurate outputs from the monitor 10.

In the embodiment shown in FIGS. 12 and 13 of the drawings, each band 18, 20 includes multiple sensing points 92, at least two of which are located anteriorly and at least two of which are located posteriorly. Thus, effectively, each band 18, 20 is divided into an anterior portion, a posterior portion and two side portions interconnecting the anterior portion and the posterior portion. Thus, using the multiple sensing points 92 and the accelerometers (not illustrated in this embodiment) to determine the position of the subject, more accurate measurements and readings are able to be obtained.

An alternative to multiple sensing points 92 is to physically divide each band 18, 20 into multiple separate segments, for example, an anterior segment, a posterior segment and two side segments. Each segment is individually calibrated and each segment is independently driven.

Thus, if any one segment of either band 18, 20 is trapped and does not extend, the remaining segments of the relevant band 18, 20 are still able to extend normally and the signal processing module 24 is able to compensate for the trapped segments of that band 18, 20.

FIG. 14 shows a further embodiment for compensating for a part of the band 18, 20 being trapped by the subject's body. In this embodiment, each band 18, 20 is carried in a segmented sleeve 94. The sleeve 94 comprises a plurality of discrete segments 96. The segments 96 are free to move axially with respect to each other but are substantially rigid in a transverse or radial direction.

Thus, if a part of the subject's body is pressed against an object, the relevant segment or segments 96 of the sleeve 94 trapped between the subject's body and the object will be held captive but the band 18, 20 is still free to extend or retract within the sleeve 94.

Figure 15:
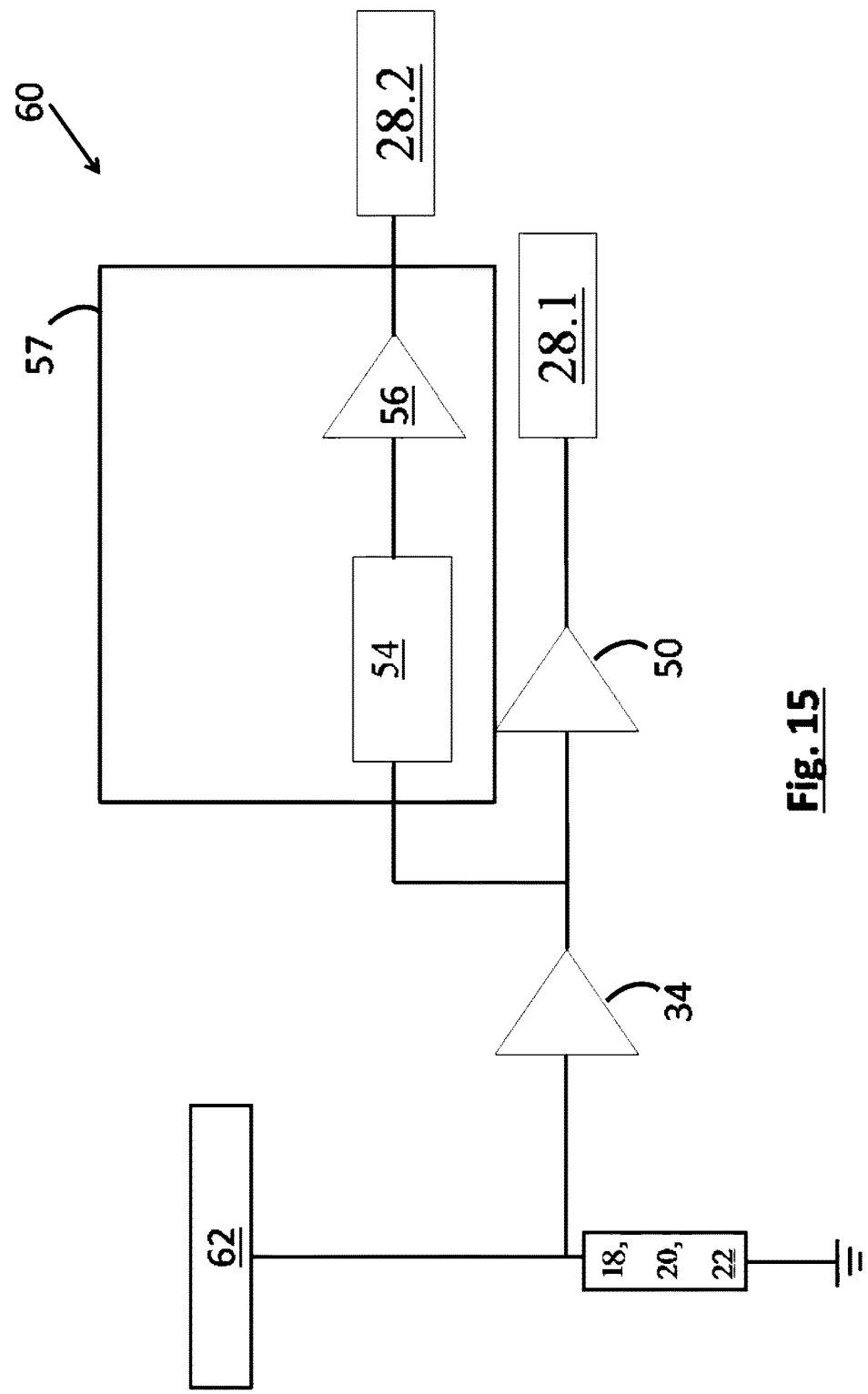
FIG. 15 shows a simplified circuit diagram of an alternative embodiment to the implementation illustrated in FIG. 3.

In FIG. 15 of the drawings, a further embodiment of the current driver arrangement for driving the bands 18, 20 and 22 is illustrated. With reference to FIG. 3 of the drawings, like reference numerals refer to like parts, unless otherwise specified.

In this embodiment, the resistor 44 is omitted. The constant current generator 62 drives the bands 18, 20 and 22 directly so the voltage drop is measured directly across the band 18, 20 or 22 instead of across the resistor 44. This results in a more sensitive circuit 60 providing more accurate output signals.

Figure 16:
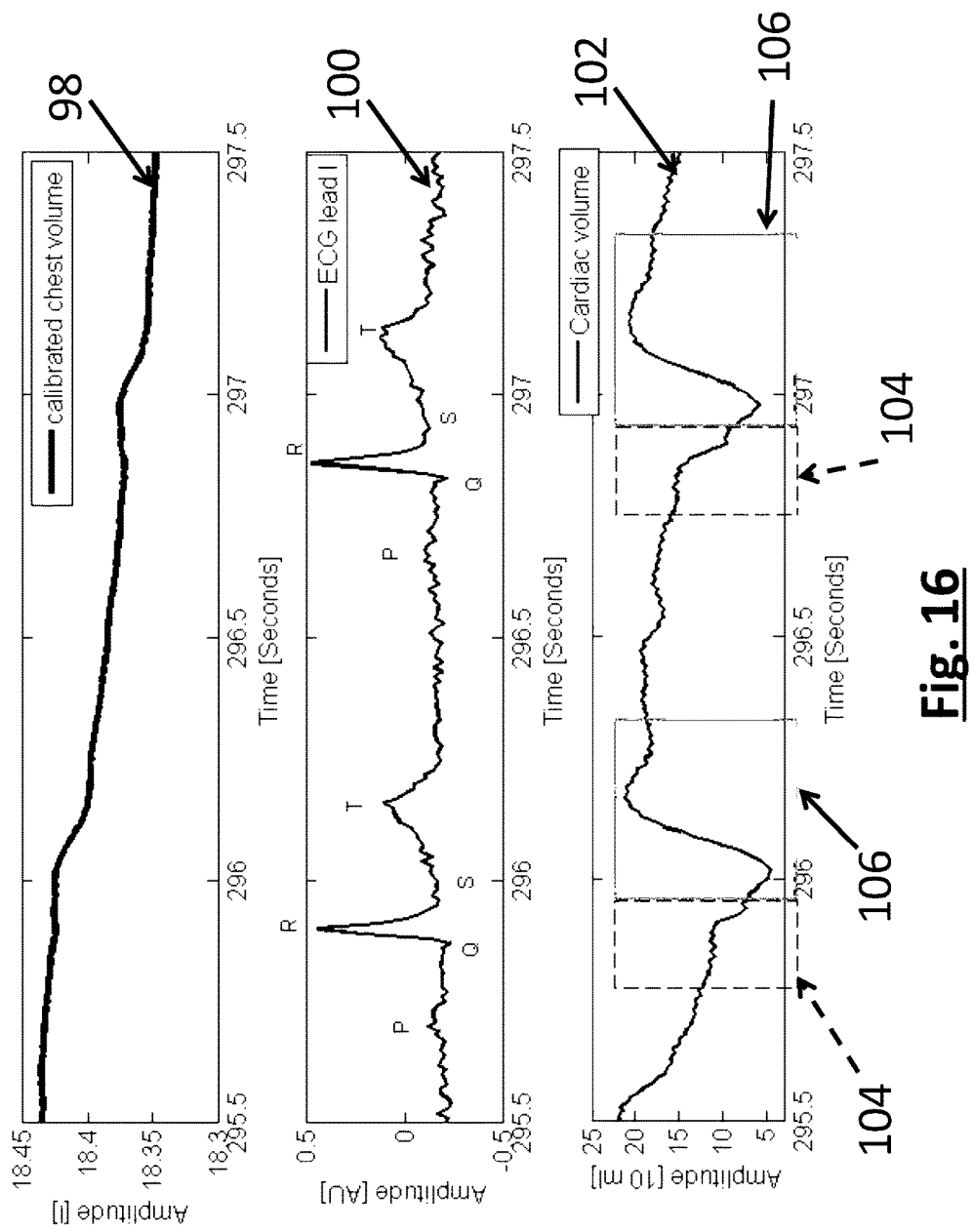
FIG. 16 shows a graphical representation of a cardiac signal extracted from the monitor.

FIG. 16 of the drawings shows a graphical representation of cardiac function of a subject wearing the monitor 10. An upper trace 98 shows the calibrated chest volume determined by the monitor 10. An ECG signal excerpt 100 is used to distinguish between stroke volumes of the cardiac chambers. Finally, a trace 102 provides cardiac stroke from the trace 98 using a wavelet. With respect to the trace 102, the part of the trace 102 bounded by the dotted line 104 represents atrial function and the part of the trace 102 bounded by the solid line 106 represents ventricular function of the subject's heart.

Figure 17:
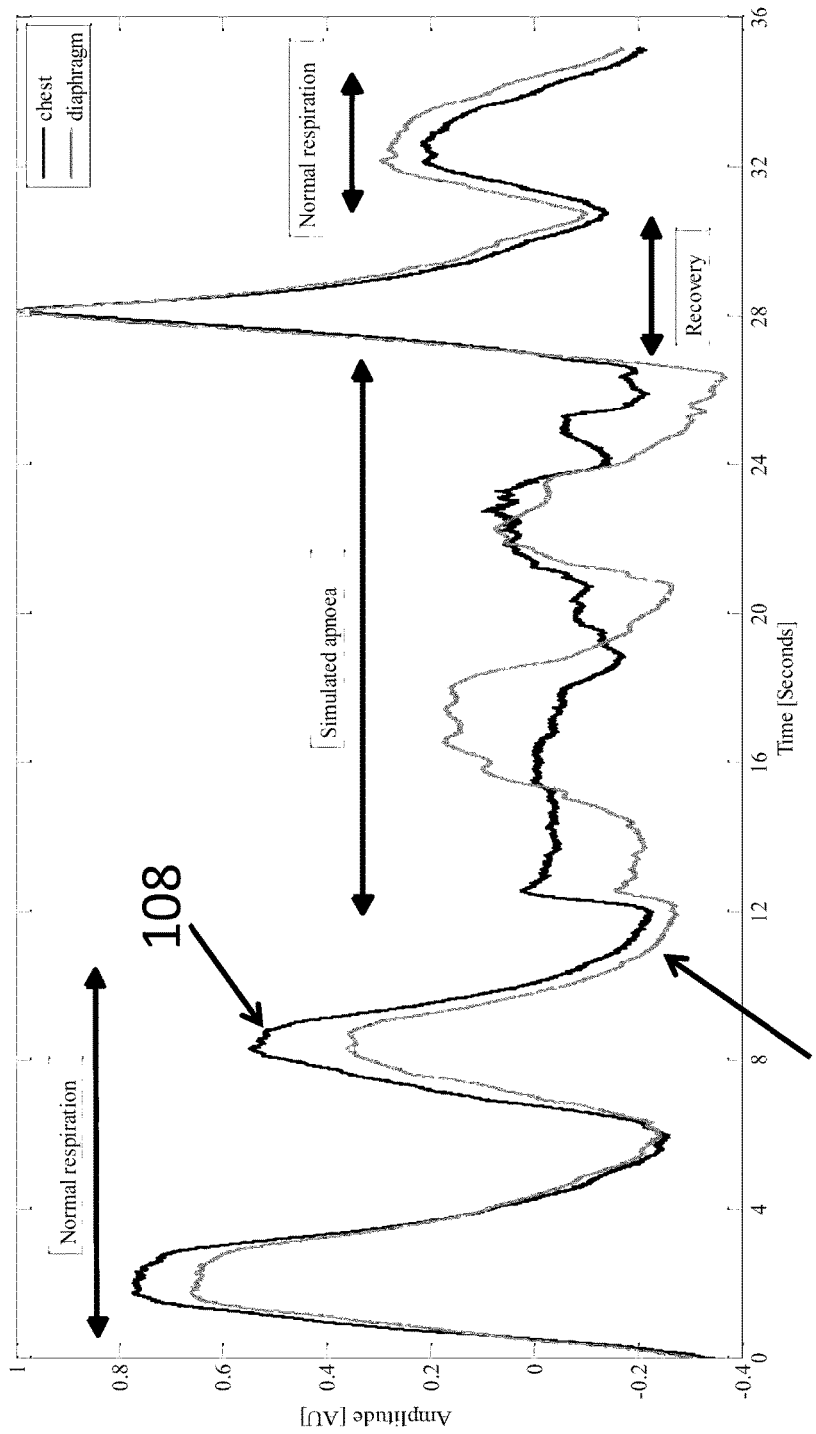
FIG. 17 shows a graphical representation of an output from the monitor for a subject suffering from sleep apnoea.

In FIG. 17 of the drawings, a graphical representation of the output from the bands 18, 20 of the sensing arrangement 16 of the monitor 10 for a subject suffering from sleep apnoea is illustrated. Trace 108 shows the chest volume as measured by band 18 and trace 110 shows the diaphragm displacement as measured by band 20.

Figure 18:
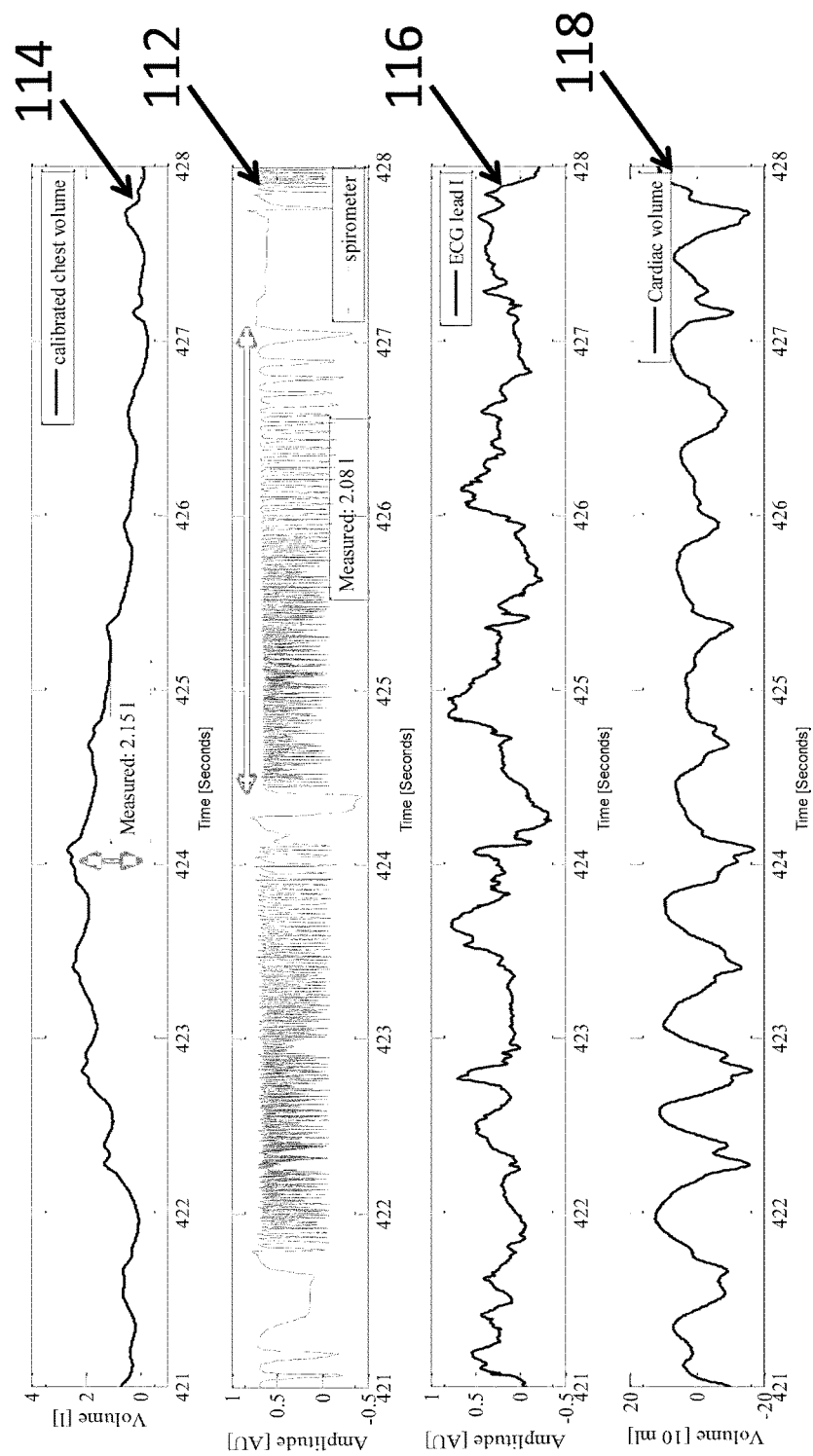
FIG. 18 shows a graphical representation of a recording made by the monitor of a subject undergoing physical activity.

In FIG. 18 of the drawings, a graphical representation of a subject undergoing physical activity is illustrated. In this embodiment, the subject is using a spirometer as shown by trace 112. Trace 114 represents calibrated chest volume as determined by the monitor 10.

Also in this embodiment, the subject is connected to an ECG to provide a reference trace 116. The trace 116 shows that the ECG is not capable of accurately monitoring cardiac function while a subject is undergoing physical activity. Instead, the monitor 10 provides a trace 118 representative of cardiac function which far more accurately depicts what occurs in a subject's heart while undergoing physical activity.

Hence, it is an advantage of the described embodiments of the disclosure that a pneumocardial monitor 10 is provided which lends itself for use in monitoring subjects with respiratory and/or cardiac abnormalities or for monitoring respiratory and/or cardiac function of a subject.

The monitor 10 is easy for a human subject to apply himself or herself or, in the case of a non-human subject, for the clinician to apply. No special skills or expertise are required in positioning the monitor 10 and the monitor 10 can be easily calibrated for use. In addition, the monitor 10 obviates the need for uncomfortable and cumbersome masks and related driving machinery in monitoring human subjects with sleep apnoea.

Further, the monitor 10 is able to be worn by the subject during activity, including intense activity such as sporting activities, without adversely impeding the subject's mobility and without causing discomfort. Hence, the monitor 10 is able to be used to monitor the subject's respiratory and cardiac function while engaged in such activities. This is extremely useful for subjects wishing to improve their sporting prowess in a particular sporting event or, more generally, to improve fitness.

The monitor 10 is also be able to be used for cardiac and/or pulmonary rehabilitation for subjects suffering from cardiac or pulmonary diseases.

It is a further advantage of the monitor 10 is that it can measure true respiratory function. This enables respiratory artefacts to be removed when one does not want those artefacts present during other monitoring procedures such as when doing x-rays. MRIs or CT scans. In other words, by using outputs from the monitor 10 in machinery doing such procedures, the respiratory artefacts are able to be taken into account to provide improved images, etc from such machinery.

It will be appreciated by persons skilled in the art that numerous variations and/or modifications may be made to the above-described embodiments without departing from the broad general scope of the present disclosure. The present embodiments are, therefore, to be considered in all respects as illustrative and not restrictive.

The invention claimed is:

1. A pneumocardial function monitor comprising:
   a carrier configured to be mounted about a thorax of a subject;
   a sensor mounted on the carrier, the sensor configured to monitor changes in volume of the thorax of the subject, the sensor comprising a plurality of sensing elements, which operate together to monitor at least respiratory function, which comprises measurement of changes in chest volume and measurement of diaphragm activation of the subject, which are used to interpret respiratory effort, wherein at least one of the sensing elements measures cardiac events based on volume changes of the thorax; and
   a signal processor in communication with the sensor configured to process signals output from the sensor, the signal processor having at least two outputs, a first output configured to transmit a first signal related to volume changes of the thorax, the first signal being related to respiratory function, and a second output configured to transmit a second signal from which volume changes of the thorax related to respiratory function have been filtered out, the second signal being related to cardiac function.

2. The monitor of claim 1, wherein the carrier is configured to insulate the sensor from the subject's skin.

3. The monitor of claim 1, wherein the sensor comprises a pair of resistive bands arranged in spaced relationship.

4. The monitor of claim 3, wherein the sensor comprises a helically arranged band carried by the carrier.

5. The monitor of claim 4, wherein the helically arranged band is an electro-resistive band.

6. The monitor of claim 3, wherein each band is of a resiliently flexible material, and wherein resistivity of the bands increasing with extension.

7. The monitor of claim 6, wherein each band is extended at rest to provide a resting resistance.

8. The monitor of claim 1, wherein the signal processor comprises a filter configured to filter out artifact signals.

9. The monitor of claim 1, wherein the signal processor comprises amplification circuitry configured to amplify signals from the sensor.

10. The monitor of claim 1, wherein the sensor comprises a position detector configured to monitor a position of the body of the subject.

11. The monitor of claim 1, wherein the sensor comprises a temperature monitor configured to monitor core temperature of the body of the subject.

12. The monitor of claim 1, wherein the sensor comprises an acoustic sensor configured to sense sounds emitted by the subject.

13. The monitor of claim 1 in which at least the first output is a directly amplified sensor output that is DC coupled.

14. A method of monitoring pneumocardial function, the method comprising:
   mounting a carrier about a thorax of a subject, the carrier mounting a sensor configured to monitor changes in volume of the thorax of the subject, the sensor comprising a plurality of sensing elements;
   using the plurality of sensing elements to measure respiratory function which comprises measurement of changes in chest volume and measurement of diaphragm activation of the subject which are used to interpret respiratory effort, wherein at least one of the sensing elements further measures cardiac events based on volume changes of the thorax;
   processing data output by the sensor; and
   outputting a first signal relating volume changes of the thorax related to respiratory function and outputting a second signal from which volume changes of the thorax related to respiratory function have been filtered out, the second signal being related to cardiac function.

15. The method of claim 14, comprising monitoring changes in resistivity of the sensors to obtain data on at least one of respiratory function and cardiac function.

16. The method of claim 14, which includes amplifying and DC coupling at least the first output signal.

\* \* \* \* \*